United States Patent [19]

Kawai et al.

[11] Patent Number: 5,679,576
[45] Date of Patent: Oct. 21, 1997

[54] GAS CHROMATOGRAPHIC ANALYSIS OF FLUOROMETHYL-1,1,1,3,3,3-HEXAFLUOROISOPROPYL ETHER

[75] Inventors: Toshikazu Kawai, Tsurugashima; Takaaki Yoshimura, Ube; Mineo Watanabe, Kawagoe; Manami Kamakura, Miyoshi, all of Japan

[73] Assignee: Central Glass Co., Ltd., Yamaguchi, Japan

[21] Appl. No.: 557,016

[22] PCT Filed: Mar. 23, 1995

[86] PCT No.: PCT/JP95/00538

§ 371 Date: Dec. 5, 1995

§ 102(e) Date: Dec. 5, 1995

[87] PCT Pub. No.: WO95/27898

PCT Pub. Date: Oct. 19, 1995

[30] Foreign Application Priority Data

Apr. 8, 1994 [JP] Japan .................. 6-071024

[51] Int. Cl.$^6$ ...................... G01N 30/02
[52] U.S. Cl. .......... 436/55; 73/23.35; 73/23.39; 95/88; 436/124; 436/126; 436/161; 568/683
[58] Field of Search ............... 436/55, 161, 124, 436/126; 422/62, 89; 73/23.35, 23.39; 95/82–84, 88; 568/683

[56] References Cited

U.S. PATENT DOCUMENTS

| | | | |
|---|---|---|---|
| 4,250,334 | 2/1981 | Coon et al. | 568/683 |
| 4,766,260 | 8/1988 | Manzer et al. | |
| 4,874,901 | 10/1989 | Halpern et al. | 568/683 |
| 4,874,902 | 10/1989 | Huang et al. | 568/683 |
| 5,390,667 | 2/1995 | Kumakura et al. | 128/205.12 |
| 5,391,579 | 2/1995 | Baker et al. | 514/722 |

OTHER PUBLICATIONS

Bito et al., "Long–duration, low–flow sevoflurane anesthesia using two carbon dioxide absorbents," Anesthesiology, vol. 81, No. 2, pp. 340–345, Aug. 1994.

Morgan et al. "A simplified gas chromatographic method for quantifying the sevoflurane metabolite hexafluoroisopropanol," Anesthesiology, vol. 80, No. 1, pp. 201–205, Jan. 1994.

W.P. Cottom and D.E. Stelz, Anal. Chem. 52(13) pp. 2073–2075, (1980) –"Determination of Hydrocarbons in Anhydrous . . . ".

(List continued on next page.)

Primary Examiner—Jeffrey Snay
Assistant Examiner—Jan M. Ludlow
Attorney, Agent, or Firm—Keck, Mahin & Cate

[57] ABSTRACT

The present invention provides a method in which organic matter in the product accompanied with a non-reacted hydrogen fluoride can be handled without damaging the apparatus, using a cross-linked cyanopropylmethylphenyl-silicone capillary column with which impurities of very small amounts can be separated, and with which non-reacted raw materials and by-products, which have a wide range of boiling points can be quantitated. The present invention further provides a process control method of a production method of fluoromethyl-1,1,1,3,3,3-hexafluoroisopropyl ether, which is characterized in that the content of a particular component in one of the following steps is determined and in that, assuming this as a variable, the treatment condition of the step is adjusted:

1) a step of reacting together 1,1,1,3,3,3-hexafluoroisopropyl alcohol, (para) formaldehyde, and hydrogen fluoride in the presence of sulfuric acid;

2) a step of contacting a crude fluoromethyl-1,1,1,3,3,3-hexafluoroisopropyl ether with an alkali aqueous solution and/or water; and 3) a step of distilling crude fluoromethyl-1,1,1,3,3,3-hexaflouroisopropyl ether

21 Claims, 1 Drawing Sheet

OTHER PUBLICATIONS

A.V. Gubarev and A.G. Surikov: C.A. 108 (4), 30834r (1986) "Chromatographic Analysis Silicon–and Fluorine– . . .".

C.B. Baddiel and C.F. Cullis; Chem. & Ind., pp. 1154–1155 (1960) –"Apparatus and Technique".

Bito et al. "Long–duration, Low–flow, Sevoflurane Anesthesia Using Two Carbon Dioxide Absorbents" Anesthesiology, vol. 81, No. 2 (1984), pp. 340–345.

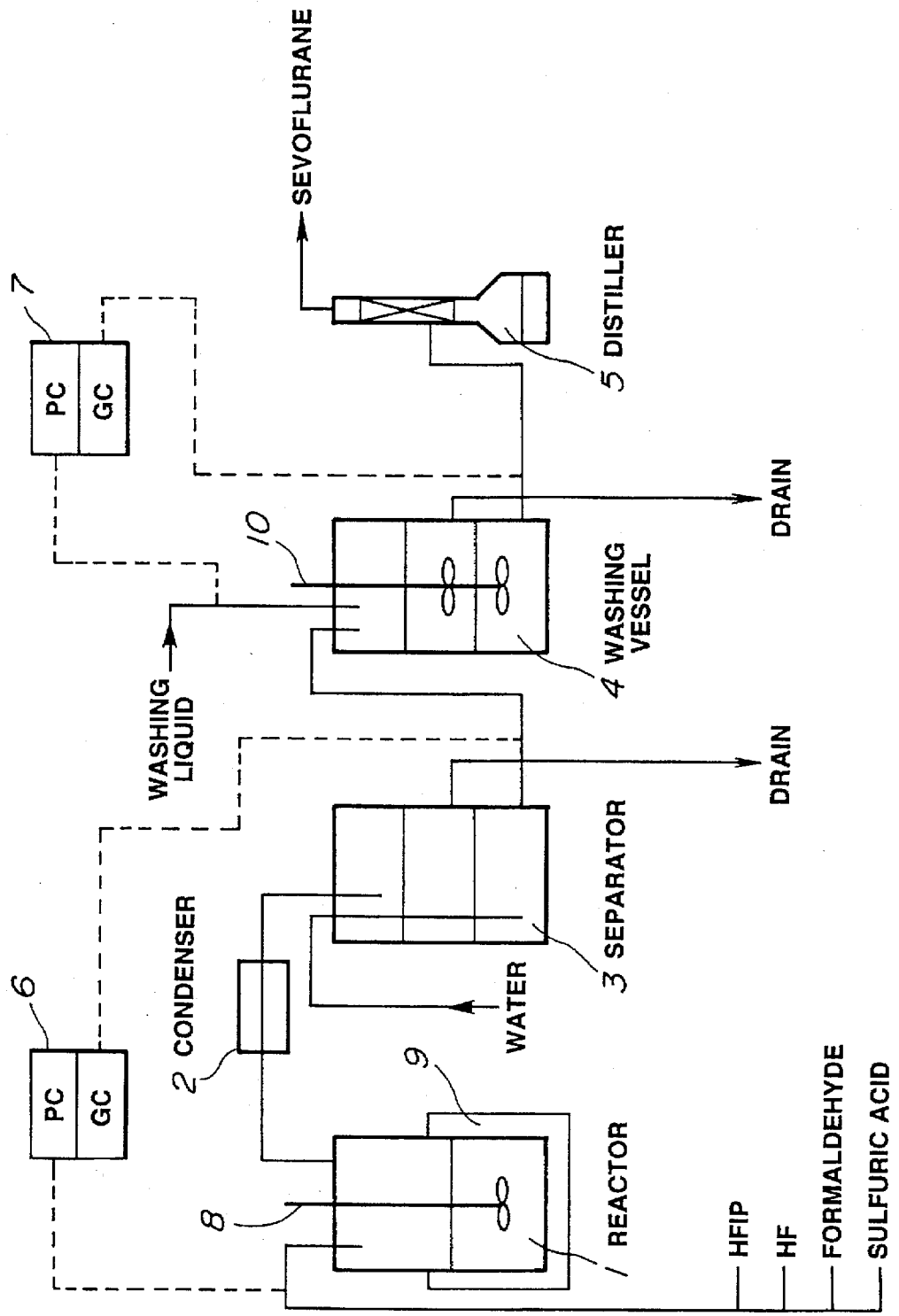

GAS CHROMATOGRAPHIC ANALYSIS OF FLUOROMETHYL-1,1,1,3,3,3-HEXAFLUOROISOPROPYL ETHER

TECHNOLOGICAL FIELD

The present invention relates to a gas chromatographic analysis of impurities in fluoromethyl-1,1,1,3,3,3-hexafluoroisopropyl ether (hereinafter referred to as "SEVOFLURANE") that is used as a pharmaceutical(s) and an agricultural chemical(s) or intermediates of these and to a monitoring of impurities by a gas chromatograph in the production process of SEVOFLURANE and a process control based thereon.

BACKGROUND TECHNOLOGY

SEVOFLURANE can be produced in accordance with a production method described in U.S. Pat. No. 4,250,334. If there is collected a gas that is generated when 1,1,1,3,3,3-hexafluoroisopropyl alcohol (hereinafter referred to as "HFIP") is added dropwise to a heated reaction mixture comprising concentrated sulfuric acid, hydrogen fluoride and paraformaldehyde, the aimed SEVOFLURANE is recovered along with the non-reacted alcohol and organic by-products such as formal, acetal and the like, which have been formed as by-products. As is frequently seen in case that such a plurality of reactions, that is, fluorination and a reaction of ether bond's formation are conducted in one pot, extremely many isomers, the reaction products of disproportionation, and the like of small amounts are formed in this reaction system, too. Of these, most of the by-products can be virtually completely removed by water washing, alkali washing, distillation and the like. However, some compounds have boiling points which are nearly the same as that of SEVOFLURANE, or behaviors of azeotropy and the like. Therefore, SEVOFLURANE as a final product may be contaminated therewith. Therefore, in view of that SEVOFLURANE is used as an inhalation anesthetic, it is necessary to strictly identify the materials and to determine their contents.

Hitherto, for the purpose of quantitating fluorine-containing compounds of relatively low boiling point, a gas chromatograph has been used with selection of various columns. For example, packed columns having chlorotrifluoroethylene oligomer as the liquid phase, such as DAIFLOIL#50 and the like, have been used at a low temperature, or there have been used columns having a porous polystyrene resin as the fixed phase, such as PORAPAK Q and the like. However, they were not sufficient as a means of microanalysis that is required for impurities of pharmaceuticals. From a viewpoint of microanalysis, the use of capillary column is effective. However, in case that capillary columns having methyl silicone, phenyl silicone and the like as the fixed phase were used, it was impossible to get a sufficient degree of separation, with respect to by-products of low boiling point which cause problems particularly to SEVOFLURANE.

Furthermore, in the process management of reaction process, purification process and the like, the objects of analysis are not necessarily only samples containing only by-products having nearly the same boiling points. It is necessary to analyze at the same time high boiling point compounds such as non-reacted raw material and the like, too. However, the above-mentioned columns were not able to meet such requirements.

Furthermore, in the production of fluorine-containing organic compounds, hydrogen fluoride (HF) is frequently used as a fluorination agent of organic compounds. For example, there is disclosed in the specification of U.S. Pat. No. 4,766,260 (1988) that tetrahaloethylene and hydrogen fluoride are reacted together in the presence of a fluorinated alumina catalyst carrying thereon nickel and the like, at a temperature from 300° C. to 450° C., thereby producing 1,1,1-trifluorodichloroethane and 1,1,1,2-tetrafluorochloroethane.

In such a case, fluorine-containing organic compounds that are un-purified or in the reaction process are intended to be analyzed by a gas chromatograph, the column and the detector are corroded by hydrogen fluoride contained in the sample. In case that hydrogen fluoride is generated by the reaction between a fluorine-containing organic compound(s) and another compound, a similar problem may be caused.

By the way, it is known that hydrocarbons of low molecular weight (methane, ethane, ethyl fluoride, propane, n-hexane, and the like) which are contained in anhydrous hydrogen fluoride and have a concentration of from 1 to 1,000 µg/g are extracted with carbon tetrachloride, followed by quantitative analysis (limit of detection 0.5 µg/g) with a gas chromatograph (W. P. Cottom, D. Z. Stelz: Anal. Chem., 52(13), 2073 (1980)).

It is disclosed in A. V. Gubarev, A. G. Surikov: C. A. 108 (4), 30834r (1986) that, when the product's flow of the decomposition reaction of silicon tetra fluoride by sulfuric acid was analyzed, using an apparatus in which each part of a commercial gas chromatograph was replaced by PTFE resin and in which the detector was coated with a fluorine-containing paint, silicon tetrafluoride was decomposed by the coexisting steam, and the formed silicon dioxide accumulated in the passage of the gas chromatograph, and thus that this apparatus can be used only for analysis of a dry gas-flow.

Furthermore, it is known that, when a halogenated methane is analyzed with a gas chromatograph equipped with a hydrogen flame ionization detector (FID), hydrogen fluoride is generated in the flame of FID, and the detector is corroded, and thus that carbon monoxide is used in place of hydrogen (C. B. Baddiel, C. F. Cullis: Chem. & Ind., 1150 (1960)).

The present invention provides a method that is capable of separating SEVOFLURANE and by-products of from low boiling point to high boiling point, using a single column, when there is analyzed, with a gas chromatograph, SEVOFLURANE containing by-products obtainable by reacting together HFIP, (para) formaldehyde, and hydrogen fluoride, in the presence of sulfuric acid.

In other words, it provides a separation column that is capable of separating very small amounts of impurities and of quantitating non-reacted raw materials and by-products, which have a wide range of boiling points, and provides a method in which organic matter in the product accompanied with non-reacted hydrogen fluoride can be handled, without damaging the apparatus, and provides a method of managing the process of production of SEVOFLURANE, with the application of these analytical methods.

DISCLOSURE OF THE INVENTION

In a method of producing SEVOFLURANE, which contains at least the following three steps, the present inventors examined a method of adjusting a treatment condition of the steps, assuming that the content of a particular component contained in crude SEVOFLURANE is a variable. With this, we found that analytical values of sufficient credibility can be obtained in the adjusting method, by using a gas chromatograph having a particular separation column and by subjecting the sample to the pretreatment. Thus, we achieved the present invention.

1) a step of reacting together HFIP, (para) formaldehyde, and hydrogen fluoride in the presence of sulfuric acid;
2) a step of contacting crude SEVOFLURANE with an alkali aqueous solution and/or water; and
3) a step of distilling crude SEVOFLURANE.

In each of the above-mentioned steps, there is an apprehension that there may be generated by-products that have boiling points near to that of SEVOFLURANE and are difficult to be separated and quantitated by a gas chromatograph. It is extremely important in the process management and the quality management to accurately identify such impurities.

The step (1) is a reaction step for synthesizing SEVOFLURANE, and various fluorinated ethers are produced as by-products. Bisfluoromethyl ether, methyl-1,1,1,3,3,3-hexafluoromethyl ether, and the like, which have boiling points near to that of SEVOFLURANE and show an azeotropic behavior together with SEVOFLURANE, are impurities that have a possibility to cause problems to SEVOFLURANE products. The reaction condition is decided mainly by the reaction temperature and the compositional ratio of each component in a reactor containing HFIP, (para) formaldehyde, hydrogen fluoride and sulfuric acid. The reaction pressure does not have a great effect on the reaction result.

Formaldehyde may be, for example, paraformaldehyde, as long as these are in the form that is usually industrially available, and these are represented by (para) formaldehyde in the present specification. Furthermore, fuming sulfuric acid, concentrated sulfuric acid or sulfuric acid having a concentration of at least 80 wt % may be used as sulfuric acid.

The reaction temperature is not critical, but preferably from about 30° to about 80° C. In particular, it is preferably from 50° to 70° C. Within this temperature range, it is possible to distill the formed SEVOFLURANE together with by-products and non-reacted raw materials, out of the reaction system. Therefore, this is preferable. In case that the reaction temperature is high, the production amount of bisfluoromethyl ether increases, depending on other conditions, too. Furthermore, if the reaction temperature is not higher than 30° C., the reaction does not actually occur. Therefore, this is not preferable.

It is necessary that an excess of hydrogen fluoride is present, as compared with HFIP. It is 1 to 20 times HFIP by mol, and preferably 6 to 10 times HFIP by mol. If it is not more than 1 times HFIP by mol, the conversion of HFIP decreases. Furthermore, even if it is not less than 20 times HFIP by mol, problems are not caused from a viewpoint of reaction. However, the flow amount of the non-reacted hydrogen fluoride will increase, or the size of the apparatus will increase. Therefore, this is not particularly advantageous. (Para) formaldehyde is 0.5–5 times HFIP by mol, and preferably 0.8–2 times HFIP by mol. If it is not more than 0.5 times HFIP, the conversion of HFIP decreases. Furthermore, if it is not less than 5 times HFIP, the amount of production of bisfluoromethyl ether increases. Therefore, this is not preferable. Furthermore, sulfuric acid is 0.5–20 times HFIP by mol, and preferably 0.9–3.0 times HFIP by mol. If it is not more than 0.5 times HFIP by mol, the reaction rate decreases. Not less than 20 times HFIP by mol is allowable. However, this is ineffective.

It is possible to decrease the formation ratios of bisfluoromethyl ether and of methyl-1,1,1,3,3,3-hexafluoromethyl ether, which are fluorinated ethers formed as by-products, by adjusting the above-mentioned reaction conditions. It is preferable to maintain bisfluoromethyl ether/SEVOFLURANE (referred to as gas chromatogram area ratio, and the same is used in the following) not more than 0.03 and methyl-1,1,1,3,3,3-hexafluoromethyl ether/SEVOFLURANE not more than 0.0003 and in particular not more than 0.00005. In other words, it is possible to determine the ratio of each component by analyzing a gas that is flowed out on the exit side of the reaction step (1), the condensed reaction product in the form of liquid, and the reaction product in the form of liquid, which is in the separator or at the exit of the same, by a gas chromatographic analysis. With this, it is possible to adjust the reaction conditions, taking the conversion of HFIP into consideration.

The step (2) is a step wherein crude SEVOFLURANE into which an acid material was incorporated by the reaction step (1) or by some reason is contacted with water or an alkali aqueous solution, thereby removing the acid component or dissolving and thus removing the non-reacted HFIP. It is usual to use an alkali metal compound(s) such as sodium hydroxide, potassium hydroxide, lithium hydroxide, sodium carbonate, sodium hydrogencarbonate, and the like. However, it is also possible to use an alkali earth metal compound(s) such as calcium hydroxide, magnesium hydroxide, and the like.

The concentration of the alkali aqueous solution used in the alkali washing is not critical. However, that from 0.01 to 10 wt % is convenient for use. Furthermore, the treatment temperature is usually about from 0° to 60° C. It is necessary to pay attention to the treatment temperature because SEVOFLURANE may be decomposed in relation to the concentration.

In this case, as a decomposition product, fluoromethyl-1,1,3,3,3-pentafluoroisopropenyl ether is formed together with other fluorinated ethers. However, fluoromethyl-1,1,3,3,3-pentafluoroisopropenyl ether has a boiling point close to that of SEVOFLURANE. Therefore, it was not possible to separate and quantitate fluoromethyl-1,1,3,3,3-pentafluoroisopropenyl ether with a gas chromatograph equipped with a usual column. However, by using an analytical method of the present invention, it becomes possible to quantitate the content of fluoromethyl-1,1,3,3,3-pentafluoroisopropenyl ether in the product, to adjust, based on this content, the amount of the alkali aqueous solution to be added, and to minimize the amount of production of fluorinated ethers which are produced as by-products. In this case, usually it is preferable to adjust fluoromethyl-1,1,3,3,3-pentafluoroisopropenyl ether/SEVOFLURANE not higher than 0.0003.

In the step (3), it suffices to conduct a usual distillation. However, it is optional to use an acid-receiving agent and a stabilizing agent for the purpose of preventing the acid generation.

In the production process of SEVOFLURANE, it is effective to further add the following step:

(4) a step of contacting crude SEVOFLURANE containing bistrifluoromethyl ether with a Brönsted acid(s), a Lewis acid(s), or an acid(s) fixed to a resin or the like (referred to acid and the like).

In the step (4), it is possible to remove bisfluoromethyl ether. As a Brönsted acid(s), a Lewis acid(s), or an acid(s) fixed to a resin or the like, which are used here, it is possible to cite, for example, sulfuric acid, fuming sulfuric acid, sulfuric acid anhydride, hydrogen bromide, hydrogen iodide, trifluoroacetic acid and trifluoromethanesulfonic acid, trifluoroboron, tetrafluorotitanium, Nafion (product of DuPont Co.), and the like. The amount of a Brönsted acid(s) and a Lewis acid(s), which are used, is 0.2 to 20 times by mol bisfluoromethyl ether contained in the crude SEVOFLURANE, and preferably 1 to 10 times bisfluoromethyl ether. If it is not more than 0.2, it is not possible to completely remove bisfluoromethyl ether. Therefore, this is not preferable. Its use in excess is not particularly limited. However, it is better that the amount for use is smaller, for easing the separation procedure and the alkali washing after the treatment by acid. The temperature to conduct this treatment is from 0° to 100° C., preferably from 10° to 60° C., and more preferably from 20° to 40° C. If it is not higher than 0° C., the treatment requires a long time. If it exceeds 100° C., a small amount of SEVOFLURANE is unfavorably decomposed. In case that the treatment is conducted at about normal pressure, it is most preferable to conduct that at a temperature from 20° to 40° C., which is about the atmospheric temperature, in respect of apparatus and of the point that the above-mentioned decomposition does not occur. In this treatment, it is preferable to adjust the treatment temperature, the treatment time, the reaction pressure, or the ratio crude SEVOFLURANE/acid and the like, in a manner to make bisfluoromethyl ether not more than 0.0001 relative to SEVOFLURANE, based on the content of bisfluoromethyl ether in SEVOFLURANE to be treated.

We examined the gas chromatographic analysis conditions and the pretreatment conditions of the sample, which capable of providing the accurate determination of the content of the fluorinated ethers contained in SEVOFLURANE, which is important in setting up the above-mentioned reaction conditions or treatment conditions. With this, we found that the separation and determination of the fluorinated ethers in the crude SEVOFLURANE, which are produced as by-products, are made possible by conducting quantitative analysis with a gas chromatograph, after, depending on the situation, previously contacting the sample with an alkali metal compound or an alkali earth metal compound, using a cross-linked cyanopropylmethylphenylsilicone capillary column.

In the production of SEVOFLURANE, HFIP as a raw material, and formal, acetal and the like as by-products have high boiling points as compared with SEVOFLURANE. Therefore, it is necessary to conduct the separation at a relatively high temperature to analyze these with a gas chromatograph. In this case, capillary columns such as methyl silicone and phenyl silicone are effective, but are unsatisfactory in separating low-boiling-point components such as bisfluoromethyl ether.

By the way, most of fluorine-containing organic compounds such as SEVOFLURANE are low-boiling-point compounds, because intermolecular interaction is small due to the peculiarity of fluorine atom. Most of by-products in the production of SEVOFLURANE are also, of course, fluorine-containing organic compounds and in most cases have characteristics analogous to those of SEVOFLURANE. Therefore, with such a column, it is impossible to determine the content of the fluorinated ethers produced as by-products, with an accuracy that is necessary for the management of the production process.

To be concrete, it is desirable, in terms of quality control and of process control, that fluoromethyl-1,1,3,3,3-pentafluoroisopropenyl ether (referred to as "analogous material 1" too in the following), methyl-1,1,1,3,3,3-hexafluoromethyl ether (referred to as "analogous material 2" too in the following), and bisfluoromethyl ether, which are analogous materials of SEVOFLURANE, are separated from SEVOFLURANE, and that HFIP as a raw material and high-boiling-point analogous materials such as acetal and formal, which are produced as by-products, can be detected at the same time.

Fused-silica capillary columns have slightly polar, medium polar, and strongly polar types, depending on the types of crosslinking agents thereof. In the case of strongly polar type, it is impossible to detect high-boiling-point analogous materials. Therefore, it is not possible to use this in the analysis of SEVOFLURANE. In the case of slightly polar type (e.g., cross-linked phenylmethylsilicone capillary column), it is difficult to separate low-boiling-point analogous materials, and in particular it is not possible at all to separate the above-mentioned analogous materials 1 and 2 under a usual gas chromatographic temperature condition. Therefore, it is necessary to improve the degree of separation by conducting the analysis particularly at a low temperature not higher than room temperature. For example, even if the analysis is conducted at 10° C., the analogous materials 1 and 2 are hardly separated. Furthermore, under such a condition, it is necessary to raise the temperature up to a high temperature for the purpose of distilling high-boiling-point materials out. As a consequence, it becomes necessary to provide an incidental device that can be used from a low temperature to a high temperature. This is uneconomical.

Therefore, one that is capable of achieving this object is limited to the medium polar column. However, it is extremely difficult to separate the analogous materials 1 and 2 even with the medium polar column, or difficult to detect the high-boiling-point analogous materials.

Furthermore, it is possible to separate the analogous materials 1 and 2 for example, with a cross-linked diisodecylphthalate capillary column which is medium polar. However, the cross-linking agent is limited in thermal stability. Therefore, it is impossible to conduct the analysis at a high temperature and thus to detect the high-boiling-point analogous materials. It is necessary in the process control and the quality control that the degree of separation between each analogous materials is at least 2.

However, we eagerly examined columns which are capable of separating, at the same time, the analogous materials, materials derived from raw materials, and the like, and SEVOFLURANE. As a consequence, we found that a cross-linked cyanopropylmethylphenylsilicone capillary column is particularly effective as a capillary column that has a degree of separation that has not been obtained by a conventional fused-silica capillary column.

Cross-linked cyanopropylmethylphenylsilicone capillary column is a capillary column in which the inside surface of the fused-silica column is coated with cyanopropylmethylphenylsilicone, followed by the cross linking thereof. It is widely applied to the analysis of trihalomethanes, chlorine-containing hydrocarbons, dioxin, chlorine-containing agricultural chemicals residue, and the like. Its commercial products are Halomatics-624 made by Quadrex Co. and the like. These can preferably be used.

The degree of separation was determined under the following analysis conditions, with respect to the analogous material 1, the analogous material 2, SEVOFLURANE, and HFIP. The results are shown in Table 1. The degree of separation is sufficiently larger than 2.0. Therefore, we find that it has a credibility that is necessary for the quality control and the process control.

Analysis Condition

Gas Chromatograph: Hewlett Packard HP-5890 series II
Column: Halomatics-624 (30 m×0.32 mm ID×3 μm)
Column Temperature: 40° C. (retention for 10 min.)–200° C. (temperature raising rate: 10° C./min.)

Injection Port Temperature: 200° C.
Carrier Gas: He 40 kPa
Sample: 0.5 μl
Split Ratio: 1/80
Detector: FID 200° C.
Integrator: Hewlett Packard HP-3396 series II

TABLE 1

| Degree of Separation | Analogous Material 2 | SEVOFLURANE | HFIP |
| --- | --- | --- | --- |
| Analogous Material 1 | 2.1 | 5.7 | 53.1 |
| Analogous Material 2 | — | 3.5 | 45.6 |
| SEVOFLURANE | — | — | 36.1 |

The degree of separation requires at least 2.0 for quantitative analysis and is represented by:

$$\text{Degree of Separation} = \frac{2X(T_1 - T_2)}{W_1 + W_2}$$

where T1 and T2 respectively represent the retention times (min.) of the material 1 and the material 2, and W1 and W2 respectively represent the peak widths (min.).

Furthermore, in general, a sample taken from the fluorination system contains hydrogen fluoride together with an organic compound(s). Therefore, a matter that requires attention, upon using a cross-linked cyanopropylmethylphenylsilicone capillary column, is that a gas chromatograph as an analytical apparatus is corroded. Of course, every part that is brought into contact with the sample is expected to have corrosion. In particular, it appears the most strikingly in the capillary column which is made of fused silica. Deterioration of the column due to corrosion is recognized as instability of the analytical values and change of the analytical values with the passage of time.

This is clearly caused by the existence of hydrogen fluoride. Therefore, a method is effective, in which it is contacted with a hydrogen fluoride fixation agent that does not react with organic compounds including the by-products and nor act as a catalyst, to remove it. It was found particularly effective that, prior to the injection of the sample into the gas chromatograph, it is contacted with an alkali metal compound(s) or an alkali earth compound(s), for the purpose of decreasing several percents of hydrogen fluoride to a level (i.e., not higher than 100 ppm) that is generally said as not having an effect on the gas chromatographic analysis.

As the alkali metal compounds, sodium fluoride (NaF, melting point: 995° C.) and potassium fluoride are preferable. As the alkali earth metal compounds, magnesium compounds such as magnesium carbonate and magnesium oxide, calcium compounds such as calcium carbonate, calcium chloride, calcium hydroxide and calcium oxide, strontium compounds such as strontium carbonate, and barium compounds such as barium carbonate are preferable.

Such a fixation method of hydrogen fluoride can be applied even if SEVOFLURANE is in the form of liquid phase or gas phase. In case of the liquid phase, it is conducted at a temperature from 0° to 60° C. In case of the gas phase, it is conducted at a temperature from 0° to 300° C. In case of the liquid phase, either the batch method or the flow method will do. In case of the gas phase, in general, the flow method can be easily used.

The mechanism of the reaction between the hydrogen fluoride fixation agent and hydrogen fluoride in case that it is the alkali metal compound is different from that in case that it is the alkali earth metal compound. In case of the alkali metal compound, it is represented by the following reaction formula.

NaF+HF→NaF.HF (solid)

On the other hand, in case of the alkali earth metal compound, it is represented by the following reaction formula.

Ca(OH)$_2$+2HF→CaF$_2$+H$_2$O

As is clear from the above reaction formulas, the necessary minimum amount of NaF is in amounts equimolar with hydrogen fluoride contained in the sample, and in case of the alkali earth metal compound it is one-half equivalent relative to HF contained in the sample. In either case, the solid phase is involved in the reaction. Therefore, it is difficult to make the hydrogen fluoride fixation agent react completely with hydrogen fluoride. Thus, it is necessary to use the hydrogen fluoride fixation agent which is in a sufficiently excess amount relative to hydrogen fluoride. Hydrogen fluoride fixation agent may be in the form of either powder, granule, or pellet. The reaction between NaF and hydrogen fluoride in the liquid phase finishes in about 1 min at room temperature. Its reaction with the alkali earth compound is almost the same. To conduct the reaction faster, the treatment vessel may be heated with a heater.

Next, the monitoring and control of the production process of SEVOFLURANE by a gas chromatographic analysis of the present invention will be exemplarily illustrated, using FIG. 1.

Sulfuric acid, formaldehyde, and hydrogen fluoride are introduced into a reactor 1 that is equipped with a stirring device 8 and a heater 9 and has a lining of PTFE. Then, the temperature of the reactor is increased. When the temperature of the reactor 1 reaches about 40° C., HFIP is introduced into the reactor 1 through a pipe, thereby starting the reaction. When the reaction starts, the temperature of the reactor 1 increases up to about 65° C. Upon this, a reaction of the following formula proceeds, thereby producing SEVOFLURANE.

(CF$_3$)$_2$CHOH+(HCHO)$_n$+HF→(CF$_3$)$_2$CHOCH$_2$F+H$_2$O

SEVOFLURANE which was formed is flowed out from the reactor together with non-reacted hydrogen fluoride, HFIP and the like, then is liquefied by a water-cooling condenser 2 that has a lining of PTFE and is maintained at about 20° C., and then is recovered by a separator 3 having a lining of PTFE.

SEVOFLURANE which was formed is added dropwise in the separator to a layer of an ion-exchange water that was injected from a pipe having a lining of PTFE. With this, most of hydrogen fluoride is removed from the organic layer, and the organic layer containing SEVOFLURANE (specific gravity: 1.54) becomes a lower layer. SEVOFLURANE in this organic layer contains about 0.1–0.2 wt % of saturated dissolved water and about 1% of hydrogen fluoride. This crude SEVOFLURANE is sent from the separator to a washing vessel through a pipe. In the middle of this pipe, a sampling opening is provided, and crude SEVOFLURANE is sampled from this sampling opening. This sampled crude SEVOFLURANE is passed through sodium fluoride in the form of granule. Then, it is analyzed by a gas chromatograph (GC) that is connected to a process controller (PC) 6 and has a cross-linked cyanopropylmethylphenylsilicone capillary column as a separation column. With this, the content of bisfluoromethyl ether and/or methyl-1,1,1,3,3,3-hexafluoromethyl ether is determined. Based on the value thereof, the amount of HFIP to be introduced is optimized by a built-in arithmetic circuit in PC, thereby setting up the degree of opening of an introducing pump of HFIP.

The organic layer as the lower layer in the separator is sent to a washing vessel 4 equipped with a stirring device 10, through the pipe having a lining of PTFE, and it is stirred and washed with a washing water (4% caustic soda aqueous solution). This crude SEVOFLURANE is sampled from a sampling opening provided at an exit of the washing vessel 4. Then, it is passed through sodium fluoride in the form of granule. Then, it is analyzed by a gas chromatograph (GC) that is connected to a process controller (PC) 7 and has a cross-linked cyanopropylmethylphenylsilicone capillary column as a separation column, thereby determining the content of fluoromethyl-1,1,3,3,3-pentafluoroisopropenyl ether. Based on the value thereof, the amount of the washing liquid to be introduced is optimized by a built-in arithmetic circuit in PC, thereby setting up the degree of opening of an introducing pump of the washing liquid.

Then, SEVOFLURANE which has been washed is introduced into a distiller 5 through a pipe having a lining of PTFE, thereby obtaining SEVOFLURANE as a main distillate, after removing a low-boiling-point component.

BRIEF DESCRIPTION OF THE DRAWINGS

FIG. 1 is an explanatory view showing an example of the production process of SEVOFLURANE.

1—Reactor, 2—Condenser, 3—Separator, 4—Washing Vessel, 5—Distiller, 6 and 7—Process Controllers, 8 and 10—Stirrers, and 9—Heater.

THE BEST MODE TO CARRY OUT THE INVENTION

Example 1

A 500 ml reactor was charged with 50 ml of 98% sulfuric acid, 100 g (5 mol) of hydrogen fluoride, and 30 g (1 mol) of paraformaldehyde. This reaction mixture was heated to 65° C. Then, 134 g (0.8 mol) of HFIP was added dropwise, over 2 hr. Vapors generated by the reaction were collected using water. With this, 140 g of crude SEVOFLURANE was obtained.

This crude fluoromethyl-1,1,1,3,3,3-hexafluoroisopropyl ether in an amount of 10 g was extracted three times with 100 ml of water, followed by an analysis with an ion chromatograph under the following conditions. With this, it was found to contain 1.2 wt % of hydrogen fluoride.
Measurement Conditions
  Ion Chromatograph: YOKOGAWA IC-7000
  Column: EXCEILPAK ICS-A35
  Thermostat Temperature: 40° C.
  Eluent: 4.4 mmol $Na_2CO_3$+1.2 mmol $NaHCO_3$ /L aqueous solution
  Removing Liquid: 15 mmol/L $H_2SO_4$ aqueous solution To this crude SEVOFLURANE, NaF pellets in amounts equivoluminal therewith were added. Then, it was allowed to stand still for 1 min. Then, it was analyzed with a liquid chromatograph under the same conditions. With this, the concentration of hydrogen fluoride was drastically decreased to 71 ppm.

Example 2

To 5 g of crude SEVOFLURANE that contains 1.2 wt % of hydrogen fluoride and has been obtained in Example 1, 0.13 g of NaF powder (1.0 times by mol the hydrogen fluoride contained therein) was added. Then, it was shaken for 30 seconds, followed by filtration. Then, it was extracted three times with 10 ml of water. Then, the concentration of hydrogen fluoride was determined under the same conditions as those of Example 1. As a result, it was 45 ppm.

Example 3

To 5 g of crude SEVOFLURANE that contains 1.2 wt % of hydrogen fluoride and has been obtained in Example 1, 0.38 g of NaF powder (3.0 times by mol the hydrogen fluoride contained therein) was added. Then, it was shaken for 30 seconds, followed by filtration. Then, it was extracted three times with 10 ml of water. Then, the concentration of hydrogen fluoride was determined under the same conditions as those of Example 1. As a result, it was 40 ppm.

Example 4

To 5 g of crude SEVOFLURANE that contains 1.2 wt % of hydrogen fluoride and has been obtained in Example 1, 0.13 g of KF powder (2.0 times by mol the hydrogen fluoride contained therein) was added. Then, it was shaken for 30 seconds, followed by filtration. Then, it was extracted three times with 10 ml of water. Then, the concentration of hydrogen fluoride was determined under the same conditions as those of Example 1. As a result, it was 35 ppm.

Example 5

To 5 g of crude SEVOFLURANE that contains 1.2 wt % of hydrogen fluoride and has been obtained in Example 1, 0.66 g of $CaCl_2$ powder (2.0 times by mol the hydrogen fluoride contained therein) was added. Then, it was shaken for 30 seconds, followed by filtration. Then, it was extracted three times with 10 ml of water. Then, the concentration of hydrogen fluoride was determined under the same conditions as those of Example 1. As a result, it was 35 ppm.

Comparative Example 1

To 5 g of crude SEVOFLURANE that contains 1.2 wt % of hydrogen fluoride and has been obtained in Example 1, 0.06 g of NaF powder (0.5 times by mol the hydrogen fluoride contained therein) was added. Then, it was shaken for 30 seconds, followed by filtration. Then, it was extracted three times with 10 ml of water. Then, the concentration of hydrogen fluoride was determined, under the same conditions as those of Example 1. As a result, it was 0.36%.

By the above treatment, the concentration of hydrogen fluoride in crude SEVOFLURANE became not higher than 100 ppm, which is considered not to interfere with the gas chromatograph. Therefore, after that, a gas chromatographic analysis of the crude SEVOFLURANE was conducted.

Example 6

SEVOFLURANE which is in an amount of 20 g and has been similarly obtained by the same reaction as that of Example 1 and 12.5 g of 4% sodium hydroxide aqueous solution were put into a 100 ml glass flask, followed by stirring with a magnetic stirrer at 40° C. over 2 hr. The thus treated crude SEVOFLURANE was analyzed under the following analysis conditions. With this, bisfluoromethyl ether was 1.5%, fluoromethyl-1,1,3,3,3-pentafluoroisopropenyl ether was 230 ppm, and methyl-1,1,1,3,3,3-hexafluoroisopropyl ether was 40 ppm. Each gas chromatogram was sufficiently separated from each other.
Analysis Conditions
  Gas Chromatograph: Hewlett Packard HP-5890 series II
  Column: Halomatics-624 (30 m×0.32 mm ID×3 μm)
  Column Temperature: 40° C. (retention for 10 min)–200° C. (temperature raising rate 10° C./min)
  Injection Port Temperature: 200° C.
  Carrier Gas: He 40 kPa
  Sample: 0.5 μl Split Ratio: 1/80
Detector: FID 200° C.
Integrator: Hewlett Packard HP-3396 series II Example 7

The crude SEVOFLURANE which contains 45 ppm hydrogen fluoride and had been treated in Example 2 was repeatedly subjected to the same analysis 30 times. With this, the decreases of the degree of separation and of sensitivity, which are considered to be caused by deterioration of column, were not found at all.

Comparative Example 2

The crude SEVOFLURANE which contains 1.2 wt % of hydrogen fluoride and had been obtained in Example 1 was analyzed under analysis conditions similar to those of Example 6, without conducting any treatment to remove hydrogen fluoride. With this, at the second time, the peak of chromatogram became broad, and thus deterioration of the column was clearly recognized. With this, the analysis was made impossible.

A gas chromatograph having a cross-linked cyanopropylmethylphenylsilicone capillary column as a separation column is extremely effective for analyzing by-products formed in the production of SEVOFLURANE. Furthermore, prior to analysis of the sample with the gas chromatograph, it is contacted with an alkali metal compound(s) or an alkali earth metal compound(s). With this, it becomes possible to make the content of hydrogen fluoride contained in the sample to an extent that the column is not virtually affected thereby. By the establishment of such an analytical method, the content of impurities in the production process of SEVOFLURANE can be extremely easily monitored. As a result of this, there is provided a remarkable advantage that SEVOFLURANE stable in quality can be obtained.

We claim:

1. A method for quantitatively analyzing a crude fluoromethyl-1,1,1,3,3,3-hexafluoroisopropyl ether containing a fluorinated ether by-product, said method comprising a step of:

(a) subjecting said crude fluoromethyl-1,1,1,3,3,3-hexafluoroisopropyl ether to gas chromatography using a cross-linked cyanopropylmethylphenylsilicone capillary column, whereby said fluorinated ether by-product is isolated and quantitatively analyzed.

2. A method according to claim 1, wherein, said crude fluoromethyl-1,1,1,3,3,3-hexafluoroisopropyl ether contains hydrogen fluoride, said crude fluoromethyl-1,1,1,3,3,3-hexafluoroisopropyl ether is contacted, prior to the step (a), with an alkali metal compound or an alkali earth metal compound, such that said hydrogen fluoride is substantially removed from said crude fluoromethyl-1,1,1,3,3,3-hexafluoroisopropyl ether.

3. A method according to claim 2, wherein said alkali metal compound is a compound selected from the group consisting of sodium fluoride and potassium fluoride, and wherein said alkali earth metal compound is a compound selected from the group consisting of magnesium carbonate, magnesium oxide, calcium carbonate, calcium chloride, calcium hydroxide, calcium oxide, strontium carbonate, and barium carbonate.

4. A method according to claim 2, wherein said crude fluoromethyl-1,1,1,3,3,3-hexafluoroisopropyl ether is contacted with said alkali metal compound or said alkali earth metal compound, at a temperature of from 0° to 60° C. under conditions that said crude fluoromethyl-1,1,1,3,3,3-hexafluoroisopropyl ether is a liquid, and a temperature of from 0° to 300° C. under conditions that said crude fluoromethyl-1,1,1,3,3,3-hexafluoroisopropyl ether is a gas.

5. A method according to claim 2, wherein a molar ratio of said alkali metal compound to said hydrogen fluoride is at least 1, and wherein a molar ratio of said alkali earth metal compound to said hydrogen fluoride is at least 0.5.

6. A method for producing fluoromethyl-1,1,1,3,3,3-hexafluoroisopropyl ether, said method comprising the steps of:

(1) reacting together 1,1,1,3,3,3-hexafluoroisopropyl alcohol, hydrogen fluoride and a member selected from the group consisting of formaldehyde and paraformaldehyde, in the presence of sulfuric acid, such that a first crude fluoromethyl-1,1,1,3,3,3-hexafluoroisopropyl ether containing a first fluorinated ether by-product is prepared;

(2) bringing said first crude fluoromethyl-1,1,1,3,3,3-hexafluoroisopropyl ether into contact with a member selected from the group consisting of an aqueous alkali solution and water, such that an acid component or said 1,1,1,3,3,3-hexafluoroiospropyl alcohol remaining after the step (1) is removed from said first crude fluoromethyl-1,1,1,3,3,3 hexafluoroisopropyl ether, and thus a second crude fluoromethyl-1,1,1,3,3,3 hexafluoroisopropyl ether containing a second fluorinated ether by-product is prepared; and (3) distilling said second crude fluoromethyl-1,1,1,3,3,3 hexafluoroisopropyl ether, thereby to produce said fluoromethyl-1,1,1,3,3,3 hexafluoroisopropyl ether, wherein at least one of an adjustment to the step (1) and an adjustment to the step (2) is conducted in said method, said adjustment to the step (1) being conducted by subjecting said first crude fluoromethyl-1,1,1,3,3,3-hexafluoroisopropyl ether to a first gas chromatography using a cross-linked cyanopropylmethylphenylsilicone capillary column, to determine a first content of said first fluorinated ether by-product, and then adjusting the step (1) depending on said first content, to decrease said first content, said adjustment to the step (2) being conducted by subjecting said second crude fluoromethyl-1,1,1,3,3,3-hexafluoroisopropyl ether to a second gas chromatography using a cross-linked cyanopropylmethylphenylsilicone capillary column, to determine a second content of said second fluorinated ether by-product, and then adjusting the step (2) depending on said second content, to decrease said second content.

7. A method according to claim 6, wherein said first fluorinated ether by-product is methyl-1,1,1,3,3,3-hexafluoroisopropyl ether, and the step (1) is adjusted by regulating a reaction temperature of the step (1), a reaction pressure of the step (1), or relative amounts of said 1,1,1,3,3,3,-hexafluoroisopropyl alcohol, one of said formaldehyde and said paraformaldehyde, and said hydrogen fluoride, such that a gas chromatogram area ratio of said methyl-1,1,1,3,3,3-hexafluoroisopropyl ether to said fluoromethyl-1,1,1,3,3,3-hexafluoroisopropyl ether, which ratio is obtained by said first gas chromatography, is maintained up to 0.0003.

8. A method according to claim 6, wherein said first fluorinated ether by-product is bisfluoromethyl ether, and the step (1) is adjusted by regulating a reaction temperature of the step (1), a reaction pressure of the step (1), or relative amounts of said 1,1,1,3,3,3-hexafluoroisopropyl alcohol, one of said formaldehyde and said paraformaldehyde, and said hydrogen fluoride, such that a gas chromatogram area ratio of said bisfluoromethyl ether to said fluoromethyl-1,1,1,3,3,3-hexafluoroisopropyl ether, which ratio is obtained by said first gas chromatography, is maintained up to 0.03.

9. A method according to claim 6, wherein, when said first crude fluoromethyl-1,1,1,3,3,3-hexafluoroisopropyl ether contains hydrogen fluoride, said first crude fluoromethyl-1,1,1,3,3,3-hexafluoroisopropyl ether is contacted, prior to said first gas chromatography, with an alkali metal compound or an alkali earth metal compound, such that said hydrogen fluoride is substantially removed from said first crude fluoromethyl-1,1,1,3,3,3-hexafluoroisopropyl ether.

10. A method according to claim 6, wherein the step (1) is conducted at a temperature of from 30° to 80° C.

11. A method according to claim 6, wherein, in the step (1), a molar ratio of said hydrogen fluoride to said 1,1,1,3,3,3-hexafluoroisopropyl ether alcohol is from 1 to 20.

12. A method according to claim 6, wherein, in the step (1), a molar ratio of one of said formaldehyde and said paraformaldehyde to said 1,1,1,3,3,3-hexafluoroisopropyl alcohol is from 0.5 to 5.

13. A method according to claim 6, wherein, in the step (1), a molar ratio of said sulfuric acid to said 1,1,1,3,3,3-hexafluoroisopropyl alcohol is from 0.5 to 20.

14. A method according to claim 6, wherein said alkali aqueous solution of the step (2) is an aqueous solution of at least one base selected from the group consisting of sodium hydroxide, potassium hydroxide, lithium hydroxide, sodium carbonate, sodium hydrogencarbonate, calcium hydroxide, and magnesium hydroxide.

15. A method according to claim 6, wherein said alkali aqueous solution of the step (2) has an alkali concentration of from 0.01 to 10 wt %, and wherein the step (2) is conducted at a temperature of from 0° to 60° C.

16. A method according to claim 6, wherein the step (1) is conducted by mixing together one of said formaldehyde and said paraformaldehyde, hydrogen fluoride, and said sulfuric acid, thereby to prepare a mixture, and then by gradually adding said 1,1,1,3,3,3-hexafluoroisopropyl alcohol to said mixture, and wherein the step (1) is adjusted by regulating a rate of addition of said, 1,1,1,3,3,3-hexafluoroisopropyl alcohol, depending on said first content of said first fluorinated ether by-product.

17. A method according to claim 6, wherein said second fluorinated ether by-product is fluoromethyl-1,1,1,3,3,3-pentafluoroisopropenyl ether, and the step (2) is adjusted by regulating a period of time of the step (2), a temperature of the step (2), or an alkali concentration of said alkali aqueous solution of the step (2), such that a gas chromatogram area ratio of said fluoromethyl-1,1,1,3,3,3-pentafluoropropenyl ether to said fluoromethyl-1,1,1,3,3,3-hexafluoroisopropyl ether, which ratio is obtained by said second gas chromatography, is maintained up to 0.0003.

18. A method according to claim 17, wherein the step (2) is adjusted by regulating the alkali concentration of said alkali aqueous solution.

19. A method according to claim 6, wherein said method further comprises a step of:

(4) bringing said first crude fluoromethyl-1,1,1,3,3,3-hexafluoroisopropyl ether obtained by the step (1) into contact with an acid selected from the group consisting of Bronsted acids, Lewis acids, and acids fixed to resins, wherein said first fluorinated ether by-product is bisfluoromethyl ether, and wherein an adjustment to the step (4) is conducted by subjecting said first crude fluoromethyl-1,1,1,3,3,3-hexafluoroisopropyl ether to a third gas chromatography by using a cross-linked cyanopropylmethylphenylsilicone capillary column, to determine a content of said bisfluoromethyl ether, and then by regulating a temperature of the step (4), a period of time of the step (4), a reaction pressure of the step (4), or a ratio of said first crude fluoromethyl-1,1,1,3,3,3-hexafluoroisopropyl ether to said acid, such that a gas chromatogram area ratio of said bisfluoromethyl ether to said fluoromethyl-1,1,1,3,3,3-hexafluoroisopropyl ether, which ratio is obtained by said third gas chromatography, is maintained up to 0.0001.

20. A method according to claim 19, wherein a molar ratio of said acid of the step (4) to said bisfluoromethyl ether is from 0.2 to 20.

21. A method according to claim 19, wherein the step (4) is conducted at a temperature of from 0° to 100° C.

* * * * *